(12) United States Patent
Waki et al.

(10) Patent No.: US 7,871,380 B2
(45) Date of Patent: Jan. 18, 2011

(54) ULTRASONIC DIAGNOSTIC APPARATUS

(75) Inventors: Koji Waki, Chiba (JP); Naoyuki Murayama, Chiba (JP)

(73) Assignee: Hitachi Medical Corporation, Tokyo (JP)

( * ) Notice: Subject to any disclaimer, the term of this patent is extended or adjusted under 35 U.S.C. 154(b) by 740 days.

(21) Appl. No.: 11/574,157

(22) PCT Filed: Aug. 23, 2005

(86) PCT No.: PCT/JP2005/015235
§ 371 (c)(1),
(2), (4) Date: Nov. 8, 2007

(87) PCT Pub. No.: WO2006/022238
PCT Pub. Date: Mar. 2, 2006

(65) Prior Publication Data
US 2008/0188743 A1   Aug. 7, 2008

(30) Foreign Application Priority Data
Aug. 25, 2004   (JP) .............................. 2004-245017

(51) Int. Cl.
*A61B 8/00* (2006.01)
*G06K 9/00* (2006.01)
(52) U.S. Cl. ...................................... 600/443; 382/307
(58) Field of Classification Search ......... 600/437–449; 382/128, 307–309
See application file for complete search history.

(56) References Cited
U.S. PATENT DOCUMENTS
6,508,768 B1 * 1/2003 Hall et al. .................... 600/443
6,558,324 B1   5/2003 Von Behren et al.
2004/0111028 A1 * 6/2004 Abe et al. .................... 600/437
2006/0052696 A1 * 3/2006 Shiina et al. ................. 600/437
2006/0052702 A1 * 3/2006 Matsumura et al. .......... 600/443
2006/0084870 A1 * 4/2006 Kim et al. .................... 600/437
2008/0051659 A1 * 2/2008 Waki et al. .................... 600/443

FOREIGN PATENT DOCUMENTS
JP   2004-057653   2/2004
JP   2004-141505   5/2004
JP   2005-027941   2/2005

* cited by examiner

*Primary Examiner*—Eric F Winakur
*Assistant Examiner*—Lawrence N Laryea
(74) *Attorney, Agent, or Firm*—Antonelli, Terry, Stout & Kraus, LLP.

(57) ABSTRACT

An ultrasonic diagnostic apparatus having a function of obtaining a tomographic image and an elastic image is adaptable to not only a close examination mode, but also a screening mode, and obtains an elastic image suitable for each examination purpose. Accordingly, the ultrasonic diagnostic apparatus of the present invention comprises tomographic image acquisition means for transmitting an ultrasonic wave from a probe to a body being examined, and receiving a reflection echo signal corresponding to the transmission of the ultrasonic wave to obtain a tomographic image, elastic image acquisition means having a first acquisition mode for determining a tissue elasticity amount of a biomedical tissue of the body being examined on the basis of the reflection echo signal to obtain an elastic image, and display means for displaying at least the elastic image. The elastic image acquisition means has a second acquisition mode different from the first acquisition mode.

18 Claims, 6 Drawing Sheets

ULTRASONIC DIAGNOSTIC APPARATUS

TECHNICAL FIELD

The present invention relates to an ultrasonic diagnostic apparatus having a function of acquiring an ultrasonic reflectance tomographic image and an tissue elastic image for a diagnosis region in a body being examined by using ultrasonic waves, and particularly to control of a mode for acquiring a tissue elastic image.

BACKGROUND ART

According to an ultrasonic diagnostic apparatus, the ultrasonic reflectance of a biomedical tissue at a diagnosis site in a body being examined is measured by ultrasonic waves and the reflectance is converted to brightness to thereby display the measurement result as a reflectance tomographic image (hereinafter abbreviated as "tomographic image") of the diagnosis site.

Furthermore, according to the ultrasonic diagnostic apparatus, it has been recently implemented that the displacement of a biomedical tissue is measured on a tomographic image which is acquired by applying a pressure variation to the biomedical tissue with a probe or the like, distortion or elastic modulus of the biomedical tissue is calculated from the spatial differentiation of the displacement concerned, or the distribution of distortion or elastic modulus in the biomedical tissue is displayed as an image (hereinafter referred to as "elastic image"). The elastic image is displayed by adding red, blue and other color information in accordance with the distortion or the elastic modulus of the biomedical tissue. By referring to this elastic image, a hard portion of the biomedical tissue is particularly made clear, and the expansion or size of tumor can be diagnosed (for example, Patent Document 1).

In general, in order to perform high-precision diagnosis, it is preferable that the elastic image has high image quality. However, much time is needed to obtain an elastic image having high image quality, and thus much time is unavoidably taken if only an elastic image of high image quality is obtained.

For example, an conventional ultrasonic diagnostic apparatus having an elastic image diagnosing function disclosed in (Patent Document 1) has only one kind of elastic image acquisition mode which is suitable to close examination, and obtains an elastic image by only the acquisition mode having high image quality and a fixed frame rate (hereinafter referred to as "high-precision mode").

However, the (Patent Document 1) pays no attention to such an acquisition mode for quickly acquiring an elastic image at a high frame rate that diagnosis can be performed in a short time (hereinafter referred to as screening mode).

Patent Document: JP-A-2005-118152

DISCLOSURE OF THE INVENTION

Problem to be Solved by the Invention

The present invention has an object to enable an ultrasonic diagnostic apparatus having a function of acquiring a tomographic image and an elastic image to be adaptable to a screening mode in addition to a close examination mode and also acquire an elastic image suitable for various examination purposes.

In order to attain the above object, an ultrasonic diagnostic apparatus of the invention comprises: tomographic image acquisition means for transmitting ultrasonic waves from a probe to a body being examined and receiving the reflection echo signal corresponding to the transmission of the ultrasonic waves to obtain a tomographic image; elastic image acquisition means having a first acquisition mode for determining a tissue elasticity amount of a biomedical tissue of the body being examined on the basis of the reflection echo signal to acquire an elastic image; and display means for displaying at least the elastic image, wherein the elastic image acquisition means has a second acquisition mode different from the first acquisition mode.

As described above, according to the ultrasonic diagnostic apparatus of the present invention, a plurality of elastic image acquisition modes are provided. Accordingly, by setting one acquisition mode suitable for a close examination mode and setting another acquisition mode suitable for a screening mode, not only the close examination mode, but also the screening mode can be adapted, and thus an elastic image suitable for each examination purpose can be obtained. As a result, the diagnosing time as a whole can be shortened.

BEST MODES FOR CARRYING OUT THE INVENTION

Preferred embodiments of an ultrasonic diagnostic apparatus according to the present invention will be hereinafter described with reference to the accompanying drawings. In all the figures for describing the embodiments of the present invention, the elements having the same functions are represented by the same reference numerals, and the duplicative description thereof is omitted.

Figure 1:
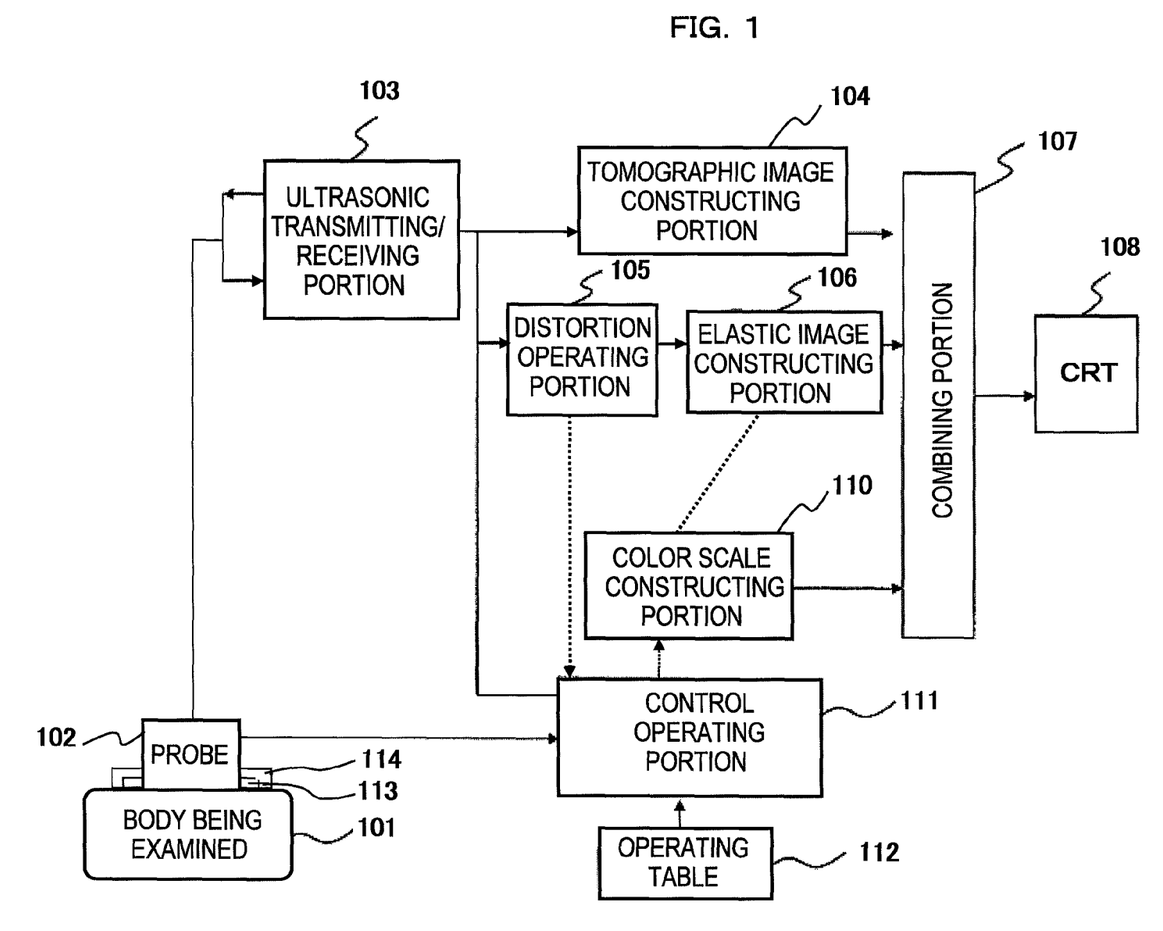
FIG. 1 is a diagram showing the whole of an ultrasonic diagnostic apparatus to which the present invention is applied.

First, an example of the ultrasonic diagnostic apparatus to which the present invention is applied will be briefly described with reference to FIG. 1. As shown in FIG. 1, the ultrasonic diagnostic apparatus includes a probe 102 used in contact with a body being examined 101, an ultrasonic transmitting/receiving portion 103 having a transmission circuit for repetitively transmitting ultrasonic waves to the body being examined 101 through the probe 102 at a time interval, a reception circuit for receiving a time-sequential reflection echo signal generated from the body being examined 101, and a phasing addition circuit for subjecting the received reflection echo to phase addition and generate RF signal data time-sequentially, a tomographic image constructing portion 104 for constructing a tomographic image of the body being examined 101 as a grayscale image, for example, a monochrome image on the basis of the RF signal data from the phase addition circuit, a distortion operating portion 105 for measuring the displacement of a biomedical tissue of the body being examined 101 from the RF signal of the phase addition circuit and determining a distortion distribution, and an elastic image constructing portion 106 for constructing a color elastic image on the basis of the distortion distribution and color scale data from a color scale constructing portion 110. Furthermore, the ultrasonic diagnostic apparatus is further provided with a combining portion 107 for combining the monochrome tomographic image and the color elastic image while changing the rate of the monochrome tomographic image and the color elastic image, and CRT 108 for displaying the composite image thus combined. Still furthermore, a control operating unit 111 for controlling the respective constituent elements is provided, and a control signal is transmitted from the control operating portion 111 to each constituent element. An operating table 112 as input means is connected to the control operating portion 111 to input an instruction from an operator, and the control operating portion 111 controls each of the constituent elements on the basis of each input.

The probe 102 is provided with plural transducers disposed therein and electrically scanned so as to form an ultrasonic wave beam to transmit ultrasonic waves to the body being examined 101, furthermore, the probe 102 receives a reflection echo signal from the body being examined 101.

The ultrasonic transmitting/receiving portion 103 has a function of setting a convergent point of plural transmitted ultrasonic waves to some depth, a function of driving the probe 102 to generate a wave-transmitting pulse for emitting an ultrasonic beam so that the ultrasonic waves are converged to the set convergent point, a function of amplifying a reflection echo signal received by the probe 102 with a predetermined gain and generating an RF signal, that is, a reception signal, and a function of subjecting plural RF signals to phase addition so that convergence is made at each of the plural convergent points, and generating RF signal data.

The tomographic image constructing portion 104 comprises a signal processor and a monochrome scan converter. The RF signal data are input from the ultrasonic transmitting/receiving portion 103 to the signal processor, and subjected to signal processing such as gain correction, log compressor, demodulation, edge enhancement, filter processing, etc. The monochrome scan comparator stores signal-processed RF signal data of one image, and converts the RF signal data concerned to a monochrome image corresponding to the display format.

The distortion operating portion 105 accumulates the RF signal data from the ultrasonic transmitting/receiving portion 103 and set the accumulated data as frame data, executes one-dimensional or two-dimensional correlation processing between frame data which are time-sequentially input at the frame rate of the ultrasonic diagnostic apparatus, and the displacement or moving vector (the direction and magnitude of the displacement) of the ultrasonic signal at each measurement point in the frame is detected to generate displacement frame data.

A block matching method and a gradient method are known as a method of measuring the moving vector. According to the block matching method, an image is divided into blocks each comprising N×N pixels, a block closest to a block being noted in the present phase frame is searched from a past phase frame, and prediction coding is carried by referring to the closed block concerned. Furthermore, according to the gradient method, each target is tracked between present phase frame and the past phase frame, and the displacement amount is calculated from the phase difference. In each embodiment of the present invention described below, the distortion operating operation 105 calculates the displacement amount by using the block matching method, however, it may calculate displacement amount by using the gradient method or other methods.

The distortion operating portion 105 calculates the distortion or the elastic modulus at each measurement point in the frame on the basis of the displacement frame data (displacement amount), generates the numeric data (elastic frame data) of the distortion or the elastic modulus, and outputs the numeric data to a gradation portion of the elastic image constructing portion 106.

Here, the distortion at the measurement point is a value obtained by spatially differentiating the displacement distribution at that point. Furthermore, pressure data input from a pressure sensor 113 through an operation controller 111 are used when the elastic modulus is calculated. Young's modulus is used as one elastic modulus, and the distortion operating portion 105 may calculate this Young's modulus Ym. Young's modulus Ym is calculated by dividing the stress (pressure) at each measurement point by the distortion value at each measurement point as shown in the following equation (1). In the following equation (1), indexes of i,j represent the coordinates of the frame data.

$$Ym_{i,j} = \{stress(pressure)_{i,j}\}/(distortion\ value\ i, j)(i,j=1, 2, 3, \ldots) \quad (1)$$

Here, the pressure applied to the surface of the body is acquired by interposing the pressure sensor 113 at the contact plane between the body surface of the body being examined 101 and a press plate 114 mounted on the probe 102 and measuring pressure data through the pressure sensor 113 by the control operating portion 111. Or, the pressure may be measured by using a method as described in Japanese Patent Application No. 2003-300325 previously filed by the applicant of this application.

The distortion operating portion 105 may execute various kinds of image processing such as smoothing processing in the coordinate plane, contrast optimizing processing, interframe smoothing processing in the time axis direction, etc. on the calculated elastic frame data, and output the processed elastic data frame as a distortion value.

The elastic image constructing portion 106 comprises a gradation portion and a color scan converter. The gradation portion, for example, rounds the distortion value data at each point in the elastic frame data input from the distortion operating portion 105 to a signal (gradation data) comprising 8 bits in order to allocate the distortion value data to gradations of 256 levels, and converted to the gradation data comprising 8 bits (256 levels). For example, data having a large distortion value is converted to a red code, and data having a small distortion value is converted to a blue code. The gradation portion outputs the converted gradation data to the color scan converter.

The color scan converter applies hue such as red color, yellow color, green color, aqua color, blue color or the like to the elastic frame data on the basis of the gradation data comprising 8 bits (256 levels) input from the gradation portion. The color scan converter colors the elastic frame data on the basis of the hue concerned and the color scale set in the color scale constructing portion 110, and outputs the colored elastic frame data as an elastic image.

The distortion and the elastic modulus are collectively referred to as an tissue elasticity amount or a tissue elastic signal.

First Embodiment

Next, a first embodiment of the ultrasonic diagnostic apparatus according to the present invention will be described. In this embodiment, the size of a correlation window for detecting the displacement amount of an ultrasonic signal between plural frames is controlled, thereby providing plural acquisition modes which are different at least in the precision of the elastic image.

In a general examination process, search and specification of a diagnostic site is carried out over a broad region in short time, and then the specified diagnostic site is subjected to close examination. According to this operating process, this embodiment is equipped with not only a close examination mode suitable for close examination of a diagnostic site, but also a screening mode suitable for search and specification of a diagnostic site over a broad region in short time as an acquisition mode for acquiring an elastic image. Furthermore, each acquisition mode may be segmentalized to provided three or more acquisition modes. Accordingly, the probe is quickly moved in the screening mode to sequentially obtain elastic images, whereby a diagnostic site is searched and specified in short time. When an affected area is found, that is, a site to be diagnosed is specified by the screening mode, the mode is subsequently switched to the close examination mode, and an elastic image having high image quality of the specified diagnostic site is obtained and supplied for precise diagnosis.

Figure 2:
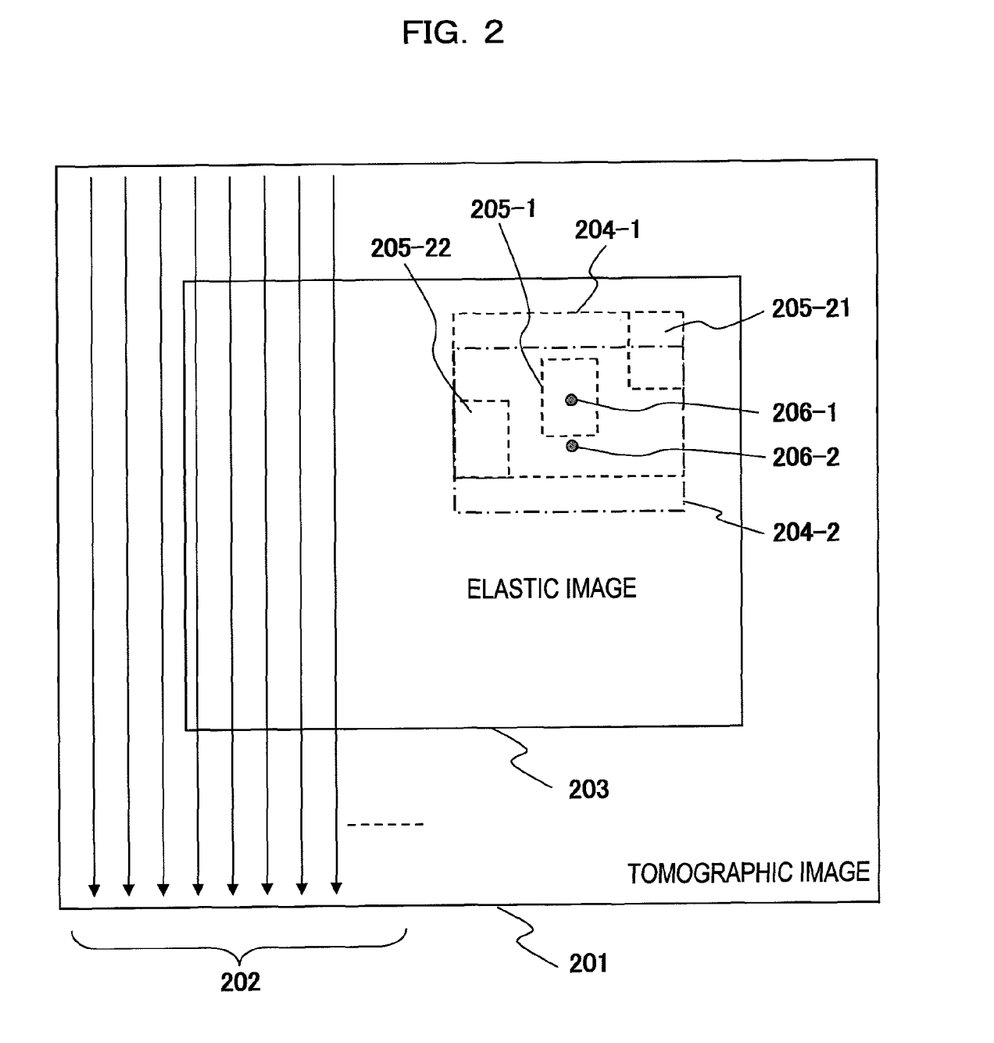
FIG. 2 is a diagram showing examples of first and second embodiments of the invention.

An example of this embodiment will be described with reference to FIG. 2. FIG. 2 shows an example in which scan lines 202 are moved in parallel by using a linear probe to acquire a tomographic image 201, and the tissue elasticity amount is calculated in the area of the tomographic image 201 to draw an elastic image 203.

In order to detect the displacement amount of an ultrasonic signal at a point 206-1, the distortion operating portion 105 sets a correlation window 205-1 containing the point 206-1 and a search range 204-1 (dashed line) in the present phase frame, and calculates the correlation value between the correlation window 205-1 and a correlation window 205-2 having the same size as the correlation window 205-1 while moving the correlation window 205-2 within the search range 204-1 in a past phase frame, thereby calculating the displacement amount of the ultrasonic signal at the point 206-1 between the two frames.

That is, the distortion operating portion 105 fixes the position of the correlation window 205-1 in the present phase frame, and calculates the correlation value of the ultrasonic signal in the correlation window 205-1 and the correlation window 205-2 between the two frames at each position while moving the correlation window 205-2 in the front-and-rear direction and in the right-and-left direction pixel by pixel within the search range 204-1 in the past phase frame. FIG. 2 shows the example in which the correlation window 205-21 at the upper right side of the search range 204-1 is moved to the correlation window 205-22 at the lower left side of the search range 204-1. Then, the difference between the position of the correlation window 205-2 in the past phase frame and the position of the correlation window 205-1 in the present phase frame when the correlation value is maximum, that is, the moving amount and the moving direction of a minute area containing the point 206-1 are set as the displacement amount of the ultrasonic signal at the point 206-1. The correlation value may be calculated while the correlation window 205-2 is fixed in the past phase frame and the correlation window 205-1 is moved within the search range 204-1 in the present phase frame.

Subsequently, the above processing is repeated while the point 206 is moved, and the displacement amount of the ultrasonic signal at each point is calculated. FIG. 2 also shows the example in which the point 206-1 is moved to the point 206-2 and a new search range 204-2 (one-dotted chain line) is set at the point 206-2.

In the above-described processing of calculating the displacement amount, when the correlation window is set to a large size, the calculation amount for calculating the correlation value is increased, and thus the calculation time required to calculate the correlation value is long. As a result, the calculation time required to determine the tissue elasticity amount is also long, so that the frame rate of the elastic image is reduced. Furthermore, when the correlation window is set to a large size, the area for calculating the correlation value is broad, so that the matching precision is enhanced. As a result, the calculation precision of the displacement amount is enhanced, and thus the precision of the elastic image is enhanced. Conversely, when the correlation window is set to a small size, the calculation amount required to calculate the displacement amount is reduced, and the frame rate of the elastic image is enhanced. However, the calculation precision of the displacement amount is reduced, and thus the precision of the elastic image is slightly reduced.

From the foregoing description, it is understood that the precision of the elastic image is controlled by controlling the size of the correlation window. Furthermore, it is also understood that the frame rate of the elastic image is also controlled by controlling the size of the correlation window. Accordingly, by controlling the size of the correlation window in accordance with an examination purpose, it is possible to control the precision and frame rate of the elastic image so that the examination purpose is properly implemented.

For example, in the screening mode, the distortion operating portion 105 preferentially enhances the frame rate by reducing the correlation window, so that the elastic image can be more easily drawn although the precision thereof is lowered, and thus the diagnosis site can be searched and specified over the broad range in short time. On the other hand, in the close examination mode, the distortion operating portion 105 gives priority to drawing of an elastic image having higher precision over the frame rate by increasing the correlation window, so that the diagnosis on the diagnostic site can be performed with higher precision.

Specifically, in the screening mode, by setting the size of the correlation window to 5 pixels×1 pixel, the frame rate of the elastic image can be set to about 60 F/S. This is a sufficient frame rate to make a general ultrasonic diagnosis. Furthermore, in the close examination mode, by setting the size of the correlation window to 30 pixels×3 pixels, a higher-precision elastic image can be drawn as compared with the screening mode. At this time, the frame rate of the elastic image is equal to about 10 F/S.

By more minutely controlling the size of the correlation window, the distortion operating portion 105 can be provided with acquisition modes which are obtained by further segmentalizing the two acquisition modes.

As described above, according to this embodiment, by controlling the size of the correlation window, plural acquisition modes which are different at least in the precision of the elastic image can be provided, and each of the acquisition modes can be selectively used in accordance with the examination purpose.

Second Embodiment

Next, a second embodiment of the ultrasonic diagnostic apparatus according to the present invention will be described. In this embodiment, the breadth of the search range for detecting the displacement amount of the ultrasonic signal is controlled among plural frames, whereby plural acquisition modes different at least in the image quality of the elastic image are provided.

As in the case of the first embodiment described above, this embodiment is also provided with plural acquisition modes containing not only the close examination mode, but also the screening mode as the acquisition mode for acquiring an elastic image, and the following description on this embodiment will be made on the basis of these two acquisition modes.

An example of this embodiment will be described with reference to FIG. 2 as in the case of the example of the first embodiment.

As described above, in order to detect the displacement amount of the ultrasonic signal at the point 206-1, the distortion operating portion 105 sets the correlation window 205-1 of the present phase frame containing the point 206-1 and the search range 204-1, and calculates the correlation value between the correlation window 205-1 and the correlation window 205-2 having the same size as the correlation window 205-1 while moving the correlation window 205-2 within the search range 204-1 in the past phase frame, thereby determining the displacement amount of the ultrasonic signal at the point 206-1 between the two frames.

In the above-described processing of determining the displacement amount, if the search range is broadened, the frequency of moving the correlation window would increase, and thus the calculation amount and the calculation time for determining the displacement amount are increased. As a result, the calculation time required to determine the tissue elasticity amount is also increased, and thus the frame rate of the elastic image is lowered. Furthermore, if the search range is broadened, the matching based on the calculation of the correlation value is carried out in a broader range, and thus a large displacement of the ultrasonic signal is captured. As a result, the calculation precision of the displacement amount is enhanced, and the artifact of the elastic image is lowered, so that the image quality is enhanced.

Conversely, if the search range is narrowed, the calculation amount to determine the displacement would decrease, and the frame rate of the elastic image would be enhanced. However, the calculation precision of the displacement amount is lowered, and thus the artifact of the elastic image is increased, so that the image quality may be lowered in some degree.

From the foregoing description, it is understood that the image quality of the elastic image, that is, the artifact amount contained in the elastic image is controlled by controlling the breadth of the search range. Furthermore, it is also understood that the frame rate of the elastic image is also controlled by controlling the breadth of the search range. Accordingly, by controlling the breadth of the search range in accordance with the examination purpose, the image quality of the elastic image (that is, the artifact amount contained in the elastic image) and the frame rate can be controlled so as to satisfy the examination purpose.

For example, in the screening mode, the distortion operating portion 105 gives priority to the enhancement of the frame rate over the image quality by narrowing the search range, so that an elastic image can be more easily drawn, and the diagnostic site can be searched and specified over the area of the broad range in short time. On the other hand, in the close examination mode, the distortion operating portion 105 gives priority to drawing of an artifact-reduced elastic image having high image quality over the frame rate by broadening the search range, so that the diagnosis on the diagnostic site can be performed with high precision.

Specifically, in the close examination mode, the frame rate of the elastic image can be set to about 60 F/S by setting the breadth of the search range to 10 pixels×1 pixel. In the close examination, an elastic image having higher image quality than that in the screening mode can be drawn by setting the breadth of the search range to 100 pixels×1 pixel. At this time, the frame rate of the elastic image is set to about 6 F/S.

By controlling the breadth of the search range more minutely, the distortion operating portion 105 can have acquisition modes which are obtained by further segmentalizing the above two acquisition modes.

As described above, according to this embodiment, by controlling the breadth of the search range, plural acquisition modes which are different at least in the image quality of the elastic image can be provided, and thus each of the acquisition modes can be selectively used in accordance with the examination purpose.

Third Embodiment

Next, a third embodiment of the ultrasonic diagnostic apparatus according to the present invention will be described. According to this embodiment, plural acquisition modes different in at least one of the spatial resolution and the frame rate of the elastic image are provided by controlling the moving interval of the search range set to detect the displacement amount of an ultrasonic signal among plural frames, that is, controlling the thinning-out of the calculation of the tissue elasticity amount.

As in the case of the first embodiment, this embodiment is provided with plural acquisition modes containing not only the close examination mode, but also the screening mode as the acquisition mode for acquiring the elastic image, and the following description of this embodiment will be made on the basis of these two acquisition modes.

A first example of this embodiment will be described. In this example, at least one of the spatial resolution and the frame rate of the elastic image is controlled by controlling the interval at which the search range 204 of FIG. 2 is moved in the scan line direction (that is, the depth direction), that is, by controlling the thinning-out manner for the calculation of the tissue elasticity amount in the scan line direction. Specifically, the control of the interval at which the search range 204 is moved in the scan line direction means the control of the thinning-out manner of thinning out the number of points at which the tissue elasticity amount is calculated in the scan line direction. That is, the broadening of the moving interval of the search range 204 means that the thinning-out amount of the calculation of the tissue elasticity amount is increased, that is, the calculation of the tissue elasticity amount is made rare. Conversely, the narrowing of the moving interval of the search range 204 means that the thinning-out amount of the calculation of the tissue elasticity amount is reduced, that is, the calculation of the tissue elasticity amount is made dense. Accordingly, the spatial resolution of the area in which the calculation of the tissue elasticity amount is made dense is enhanced, and conversely the spatial resolution of the area in which the calculation of the tissue elasticity amount is made rare is lowered.

Figure 3:
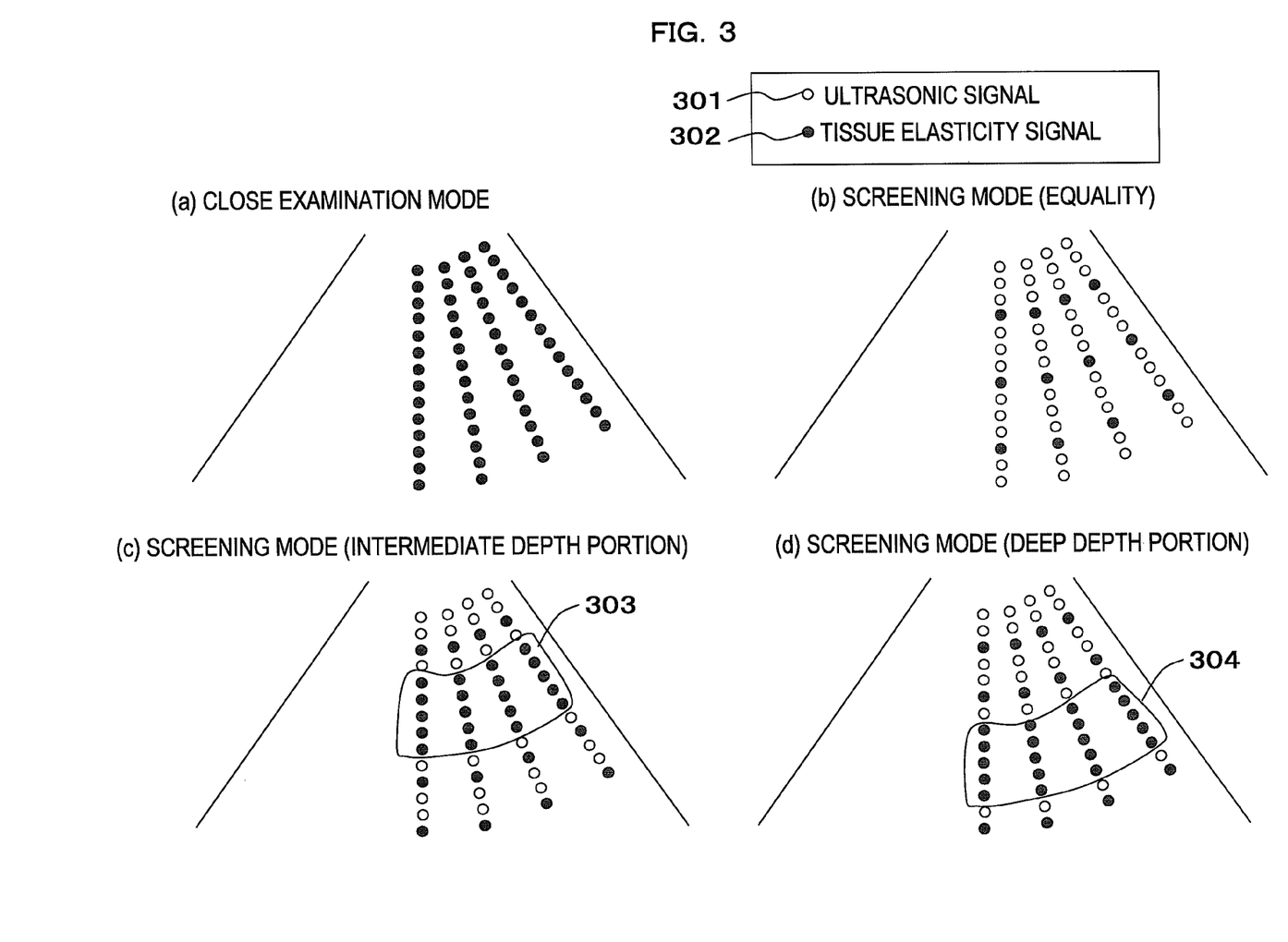
FIG. 3 is a diagram showing a first example of a third embodiment of the invention.

An example will be described with reference to FIG. 3. FIG. 3 shows an example in which at least one of the spatial resolution and the frame rate of the elastic image is made different between the screening mode and the close examination mode by changing the way of thinning out points in the scan line direction at which the tissue elasticity amount is calculated. Reference numeral 301 of FIG. 3 represents an ultrasonic signal, and reference numeral 302 represents a tissue elasticity signal reflecting the calculated tissue elasticity amount.

FIG. 3(*a*) shows an example of the way of thinning out the points at which the tissue elasticity amount is calculated in the close examination. In the close examination mode, an elastic image having high spatial resolution is preferable, and thus the elastic image constructing portion 106 calculates the tissue elasticity amount by using all the ultrasonic signals on the scan lines. That is, the elasticity image constructing portion 106 detects the displacement of the ultrasonic signal between the front and back frames every ultrasonic signal on the scan line to determine the tissue elasticity amount and construct an elastic image. Accordingly, the spatial resolution of the elastic image in the close examination mode as described above is enhanced. However, an enormous calculation amount is needed to calculate the tissue elasticity amount at each point, and further the tissue elasticity amount is calculated for each of all the ultrasonic signals on the scan lines, so that the frame rate of the elastic image in the close examination mode is lowered. Specifically, in this close examination mode, the frame rate is equal to about 15 F/S.

On the other hand, in the screening mode, the elastic image constructing portion 106 enhances the frame rate of the elasticity image by reducing the calculation amount for constructing the elastic image by thinning out the number of points at which the tissue elasticity amount is calculated, whereby the diagnostic site is searched and specified in short time. However, in the screening mode, the spatial resolution in an area where the calculation of the tissue elasticity is thinned out is lowered. FIGS. 3(*a*) to (*d*) show specific examples of the screening mode in which priority is given to the enhancement of the frame rate as described above.

FIG. 3(*b*) shows the screening mode (equality) in which the calculation of the tissue elasticity amount is thinned out at an equal interval in the scan line direction.

In this mode, the elastic image constructing portion 106 selects any one point of four points of ultrasonic signals on the scan line, and calculates the tissue elasticity amount at that point. Accordingly, in the screening mode (equality), the elastic image constructing portion 106 can construct an elastic image of one frame by the quarter signal processing amount as compared with the close examination mode shown in FIG. 3(*a*). That is, in the screening mode (equality), the frame rate of the elastic image is enhanced, and the display of the elastic image is renewed in short time. However, the spatial resolution of the elastic image in the screening mode (equality) is reduced, and it is equal to substantially a quarter of the close examination mode described above.

In the example of FIG. 3(*b*), the thinning-out operation is carried out so that one point of the four ultrasonic signal points on the scan line is selected, and only the tissue elasticity amount at that point is calculated. However, the selection of the ultrasonic signal points on the scan line at which the calculation of the tissue elasticity amount is carried out may be carried out at the thinning-out rate of one point in three points, one point in two points or the like. Furthermore, the thinning-out is not unnecessary to be carried out at the equal interval on the scan line, and quarter points or the like within a frame are randomly selected, and the tissue elasticity amount at these points may be calculated.

FIG. 3(*c*) shows the screening mode (intermediate depth portion) in which the tissue elasticity amount is densely calculated at an intermediate depth portion 303 on the scan line, and the tissue elasticity amount is rarely calculated at a shallow depth portion and a deep depth portion.

In the screening mode (intermediate depth portion), the elastic image constructing portion 106 calculates the tissue elasticity amount at sequential five points in the scan line direction at the intermediate depth portion 303, and the tissue elasticity amount is not calculated at one point adjacent to the point group at which the tissue elasticity amounts are calculated, that is, this point is skipped, and then the tissue elasticity amount is further calculated at one point adjacent to the one point concerned. Then, the tissue elasticity amount is not calculated at sequential two points adjacent to the point concerned, that is, these points are skipped, and then the tissue elasticity amount is calculated at one point adjacent to these two points. As described above, the elastic image constructing portion 106 gradually rarefies the calculation frequency of the tissue elasticity amount as the calculation position is shifted from the intermediate depth portion 303 to the shallow depth portion or the deep depth portion. Accordingly, even in the screening mode (intermediate depth portion), an elastic image of one frame is constructed by a smaller signal processing amount as compared with the close examination mode shown in FIG. 3(*a*), and thus the frame rate of the elastic image is enhanced. Furthermore, the spatial resolution in the area where the calculation of the tissue elasticity amount is made rare is lowered, however, the spatial resolution in the area where it is made dense is set to the same level as the close examination mode shown in FIG. 3(*a*).

In general, the screening mode (intermediate depth portion) in which drawing is carried out so that a diseased tissue such as cancer or the like is located at the intermediate depth portion and thus the tissue elasticity amount is mainly densely calculated at the intermediate portion of the tomographic image to thereby provide high spatial resolution is advantageous to the diagnosis.

FIG. 3(*d*) shows the screening mode (deep depth portion) in which the tissue elasticity amount is densely calculated at the deep depth portion 304 on the scan line and the tissue elasticity amount is rarely calculated at the shallow depth portion and the intermediate depth portion.

In the screening mode (deep depth portion), the elastic image constructing portion 106 calculates the tissue elasticity amount at sequential five points in the scan line direction at the deep depth portion, the tissue elasticity amount is not calculated at one point adjacent to the point group at which the tissue elasticity amounts are calculated, that is, this point is skipped, and the tissue elasticity amount is calculated at one point adjacent to the point concerned. As described above, the elastic image constructing portion 106 gradually rarefies the calculation frequency of the tissue elasticity amount as the calculation position is shifted from the deep depth portion to the shallow depth portion. The tissue elasticity amount 302 may be set so as not to be calculated at the shallow depth portion. Accordingly, even in the screening mode (deep depth portion), the elastic image of one frame is constructed by a smaller signal processing amount as compared with the close examination mode shown in FIG. 3(*a*), and thus the frame rate of the elastic image is enhanced. Furthermore, as in the case of the screening mode (intermediate depth portion), the spatial resolution in the area where the calculation of the tissue elasticity amount is made rare is lowered, however, the spatial resolution in the area where it is made dense has the same level as the close examination mode shown in FIG. 3(*a*).

Conversely to the screening mode (deep depth portion), the screening mode (shallow depth portion) in which the calculation frequency of the tissue elasticity amount is made gradually rarer from the shallow depth portion to the deep depth portion may be used.

In the area where the calculation frequency of the tissue elasticity amount is made rare, the tissue elasticity amount at a point where the tissue elasticity amount is not actually calculated is calculated by the interpolation using the tissue elasticity amounts calculated in the neighborhood of the point concerned. The calculation amount of the interpolation processing is remarkably smaller than that of the actual calculation of the tissue elasticity amounts, and thus it does not affect the frame rate of the elastic image.

The tissue elasticity amount may be calculated while sequentially switching the screening mode among the screening mode (intermediate depth portion), the screening mode (deep depth portion) and the screening mode (shallow depth portion). By the sequential switching operation as described above, the elastic image constructing portion 106 can display the elastic image of the overall frame while enhancing the frame rate.

Or, the area where the tissue elasticity amount is densely calculated or rarely calculated may be moved according to an input from an operation table 112 of an operator. For example, when the operator wants to calculate the tissue elasticity amount densely at a shallower depth portion, dense areas 303 and 304 are moved upwardly in the scan line direction. Conversely, when the operator wants to calculate the tissue elasticity amount densely at a deeper depth site, the dense areas 303 and 304 are moved downwardly in the scan line direction. In connection with the movement of the dense areas 303, 304, the calculation frequency of the tissue elasticity amount is made gradually rare as the calculation position shifts from the dense areas 303, 304 after the movement to the shallow depth portion or the deep depth portion. In the above-described example, the dense areas 303, 304 are moved. However, conversely, rare areas other than the dense areas 303, 304 may be moved.

As described above, the area where the tissue elasticity amount is densely calculated or the area where the tissue elasticity amount is rarely calculated is moved on the tomographic image, whereby this embodiment can also flexibly deal with a case where the positions of diagnostic sites are different like abdomen, prostate, etc. or the depth at which the tissue elasticity amount is densely calculated is varied, and the construction and display of the elastic image at a high frame rate can be performed in the screening mode.

As described above, by thinning out the calculation of the tissue elasticity amount in the scan line direction, the screening mode having the enhanced frame rate can be implemented and thus the diagnostic site can be searched and specified in short time.

Next, a second example of this embodiment will be described. In this example, at least one of the spatial resolution and the frame rate of the elastic image is controlled by controlling the interval at which the search range 204 of FIG. 2 is moved in a raster direction (the direction substantially perpendicular to the scan line direction), that is, by controlling the thinning-out of the calculation of the tissue elasticity amount in the raster direction. The control of the interval at which the search range 204 is moved in the raster direction specifically means the control of the thinning-out way in which the number of points at which the tissue elasticity amount is calculated is thinned out in the raster direction. Accordingly, in this example, the spatial resolution in the area where the calculation of the tissue elasticity amount is made dense is enhanced, and the spatial resolution in the area where the calculation of the tissue elasticity amount is made rare is lowered as in the case of the first example.

Figure 4:
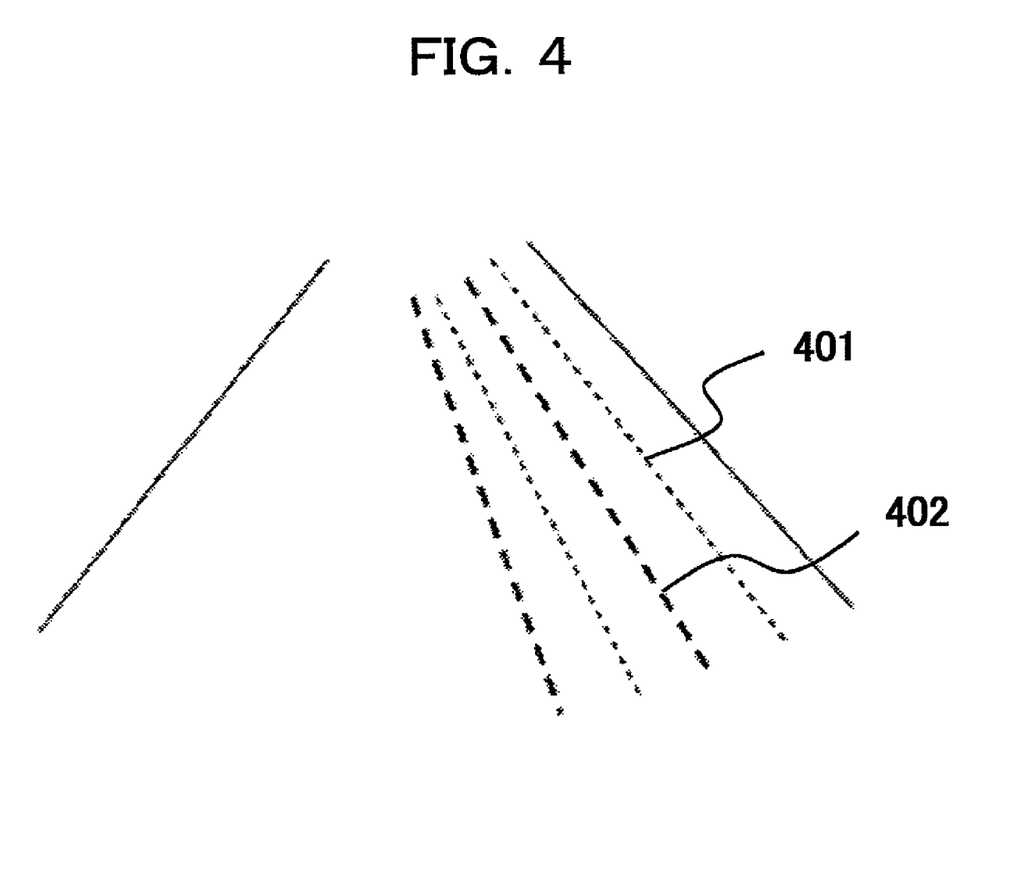
FIG. 4 is a diagram showing a second example of a third embodiment of the invention.

This example will be described with reference to FIG. 4. FIG. 4 shows a screening mode in which the calculation of the tissue elasticity amount is thinned out in the raster direction on a tomographic image acquired by a convex type probe. A scan line on which the tissue elasticity is calculated is represented as a scan line 401, and a scan line on which the tissue elasticity is not calculated is represented as a scan line 402. The example shown in FIG. 4 corresponds to a screening mode in which the calculation of the tissue elasticity amount on one scan line of the two ultrasonic scan lines is thinned out. However, the calculation of the tissue elastic amount of one scan line may be thinned out every three or more scan lines in place of two scan lines. As described above, the frame rate of the elastic image can be enhanced. However, the spatial resolution in an area in the neighborhood of the scan line on which the calculation of the tissue elasticity amount is thinned out is lowered. That is, as the rate of the scan lines on which the calculation of the tissue elasticity amount is thinned out is increased, the frame rate of the elastic image is enhanced, however, the spatial resolution is conversely lowered.

As another example of the thinning-out way of the calculation of the tissue elasticity amount in the raster direction, the calculation density of the tissue elasticity amount may be made dense (that is, the thinning-out in the raster direction is made rare) at the center portion of the frame while the calculation frequency of the tissue elasticity amount is made gradually rarer (that is, the thinning-out in the raster direction is made denser) as the calculation position shifts to both the ends of the frame. Or, the calculation frequency of the tissue elasticity amount may be dense in the area at one side of the frame while the calculation frequency of the tissue elasticity amount is made gradually rarer as the calculation position shifts to the area at the opposite side of the frame. The calculation of the tissue elasticity amount may be made gradually rarer, and finally not carried out.

As in the case of the first example, the tissue elasticity amount on a scan line on which the calculation of the tissue elasticity amount is thinned out is calculated by the interpolation using the tissue elasticity amounts on neighboring scanning lines on which the tissue elasticity amounts are actually calculated. The interpolation processing has substantially no effect on the frame rate as in the case of the first example.

As described above, by thinning out the calculation of the tissue elasticity amount in the raster direction, the screening mode having the enhanced frame rate can be implemented, and the diagnostic site can be searched and specified in short time.

Furthermore, the diagnostic site can be searched and specified in short time and the diagnostic site can be diagnosed with high precision as in the case of the above first example shown in FIG. 3 by switching the close examination mode shown in FIG. 3(a) and the screening mode in which the calculation of the tissue elasticity amount is thinned out in the raster direction according to this example.

Furthermore, the screening mode based on the thinning-out in the scan line direction of the first example and the screening mode based on the thinning-out in the raster direction of the second example may be mixed with each other so that these modes can be freely switched to each other. For example, the screening modes shown in FIG. 3(b) and FIG. 4 may be alternately switched to each other, whereby the thinning-out operation in the scanning direction and the thinning-out operation in the raster direction are alternately carried out. Or, the thinning-out operation in the scan line direction and the thinning-out operation in the raster direction may be carried out at the same time. In this case, the thinning-out operations of the calculation of the tissue elasticity amount in both the scan line direction and the raster direction are substantially equally carried out, and the image quality of the elastic image can be made isotropic.

In the screening modes of the respective examples that can enhance the frame rate, the frame rate can be enhanced to about 25 to 30 F/S, and the frame rate which is about 1.5 times as high as the close examination described above can be implemented.

Here, the effect of the enhancement of the frame rate will be described. For example, in such a case that a tissue is roughly pressed, the tissue may be displaced beyond the search range 204 shown in FIG. 2. In such a case, the displacement of the ultrasonic signal is not detected through the correlation window 205 or it is misidentified that the ultrasonic signal is displaced to a different position. In both the cases, the tissue elasticity amount is not calculated or an erroneous tissue elasticity amount is calculated.

Therefore, by enhancing the frame rate in the screening mode described above, the time interval between two frames which are adjacent to each other on the time axis is shortened. Therefore, the displacement interval of the tissue within the time interval is shortened, and thus the displacement of the ultrasonic signal is within the search range 204. Accordingly, even when an ultrasonic signal quickly displaces, the displacement of the ultrasonic signal can be captured within the search range 204, and thus the calculation precision of the tissue elasticity amount can be enhanced. That is, even when a biomedical tissue is quickly moved by rough press, the tissue elasticity amount can be calculated with high precision and an elastic image can be constructed.

When a tumor site such as cancer or the like is found in the screening mode having a high frame rate, the screening mode is switched to the close examination mode to carry out the close examination of the tumor site. This switching operation is carried out by the elastic image constructing portion 106 on the basis of an input instruction from the operating table 112, for example. By switching the screening mode to the close examination mode, the operator can find a diagnostic site, obtain a highly fine hardness distribution of the diagnostic site and accurately diagnose the diagnostic site in short time.

Figure 6:
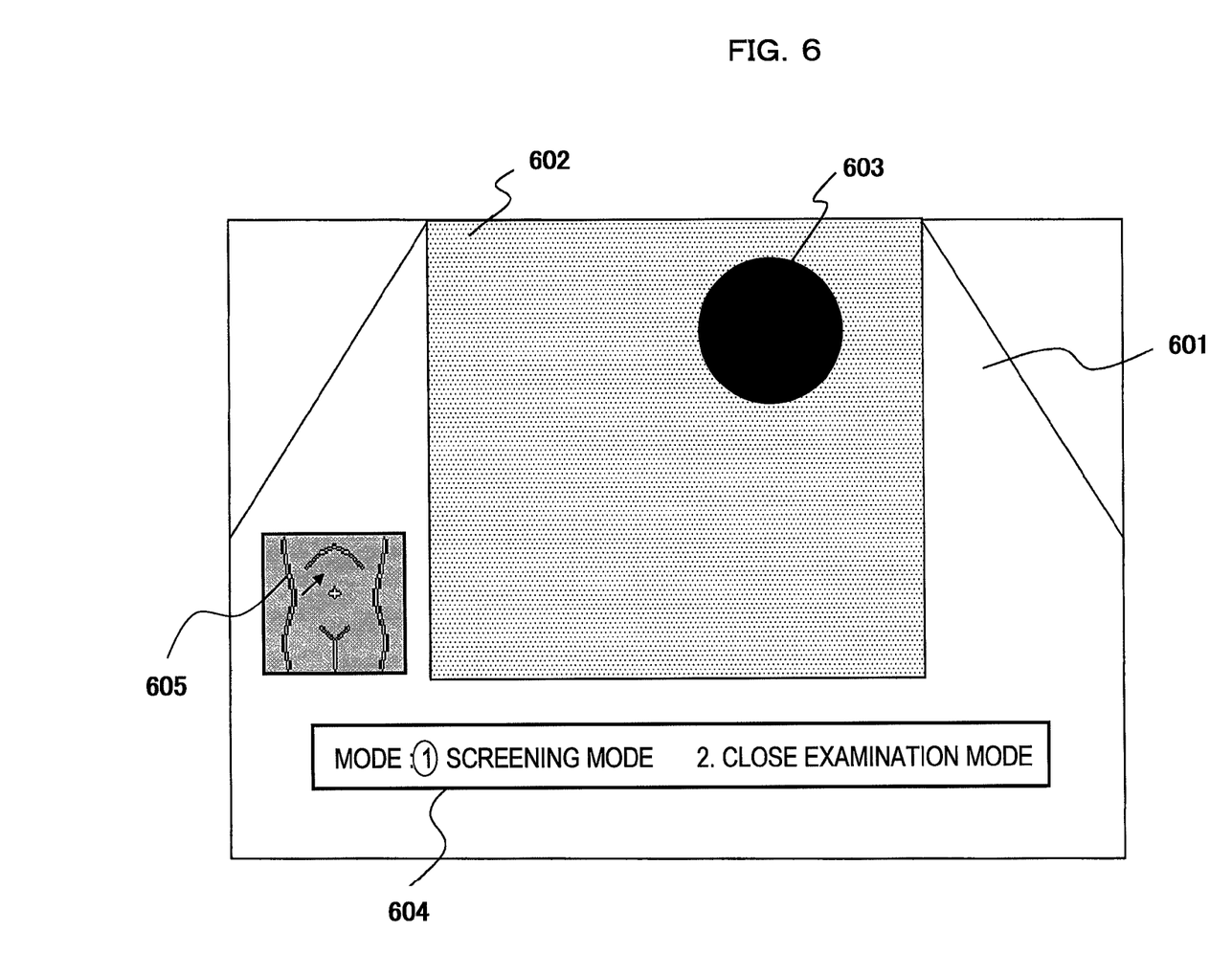
FIG. 6 is a diagram showing an example of switching means of an acquisition mode.

FIG. 6 shows an example of the acquisition mode switching operation. FIG. 6 shows the example in which a frame 602 for calculating an elastic image is set within a tomographic image 601 obtained by a convex type probe and the elastic image is displayed in the frame 602. 603 represents cancer as an example of a solid tissue, and the elastic image 602 is represented with different hue so that the hardness of the area of the cancer 603 is identified. In this example, a menu for selecting the screen mode and the close examination mode is displayed on the screen, and any menu is selected to select the corresponding acquisition mode. The selection of the acquisition mode is carried out on the basis of an input instruction from the operating table 112, for example. The acquisition mode being selected is represented by a circle 604. Or, the character sequence of the acquisition mode concerned may be represented in a high-light display style. In FIG. 6, it is shown that the screening mode 1 is selected. At this time, the elastic image is drawn in the screening mode described in any of the above-described embodiments. On the other hand, when the close examination mode 2 is selected, the elastic image is drawn in the close examination mode described in any one of the above-described embodiments.

As described above, according to this embodiment, plural acquisition modes which are different in at least one of the spatial resolution and the frame rate of the elastic image can be provided by controlling the moving amount of the search range set to detect the moving amount of the ultrasonic signal between plural frames, that is, by controlling the way of thinning-out the calculation of the tissue elasticity amount in at least one of the scan line direction and the raster direction, and the acquisition modes can be selectively used in accordance with the examination purpose.

Fourth Embodiment

Next, a fourth embodiment according to the ultrasonic diagnostic apparatus according to the present invention will be described. In this embodiment, when an output elastic image is constructed by using plural time-sequential original elastic images, there are provided plural modes which are different in at least one of the image quality and the frame rate of the output elastic image.

In this embodiment, as in the case of the first embodiment, plural acquisition modes containing not only the close examination mode, but also the screening mode are provided as the acquisition mode for acquiring the elastic image, and the following description of this embodiment will be also made by using these two acquisition modes.

An example of this embodiment will be described with reference to FIG. 5. In order to smoothly displaying a video of elastic images, the elastic image constructing portion 106 constructs an output elastic image on the basis of the calculation using time-sequential original elastic image data of several past frames by using an FIR filter or IIR filter.

Figure 5:
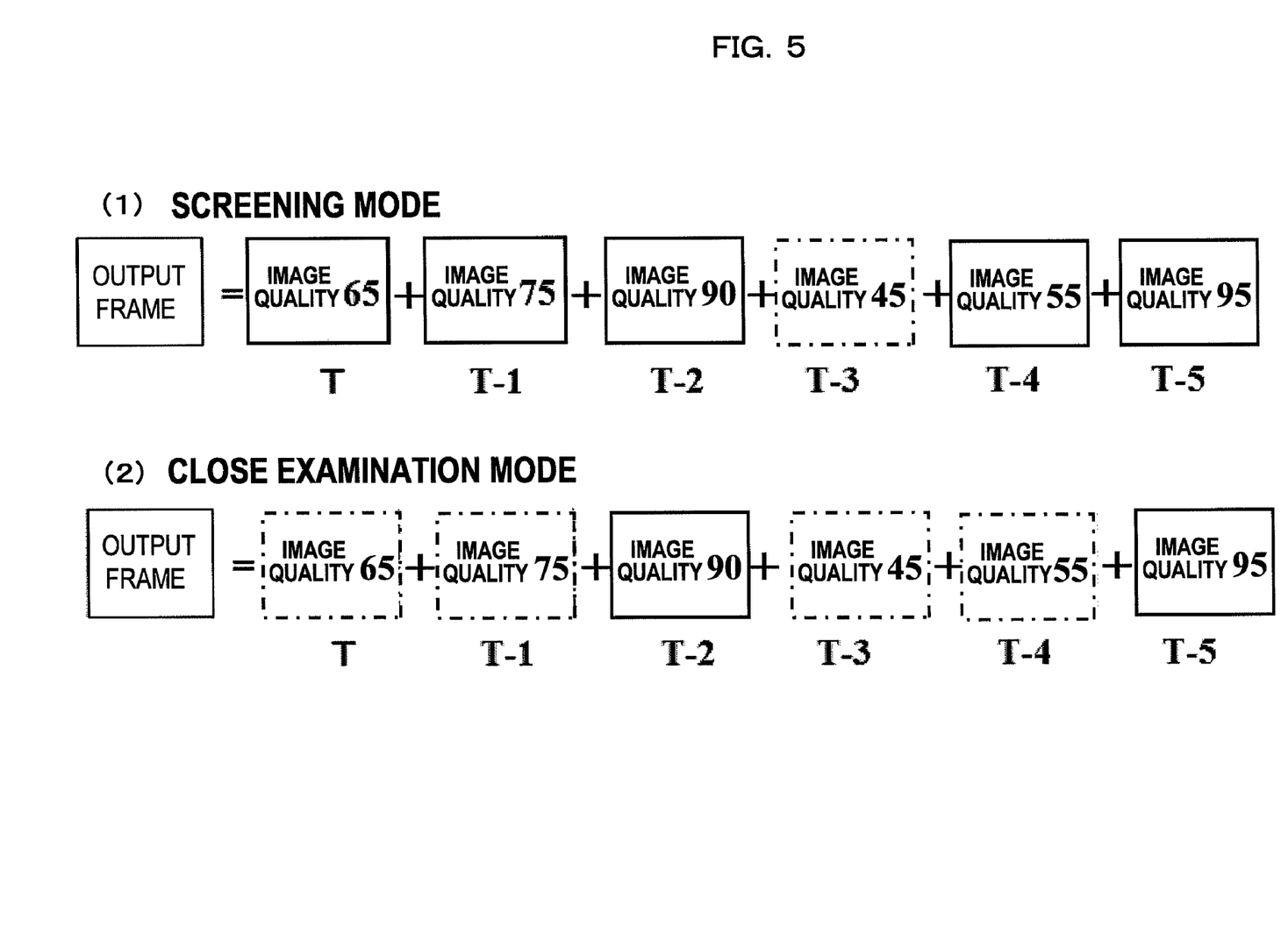
FIG. 5 is a diagram showing a fourth embodiment of the invention.

FIG. 5 shows an FIR filter system constructing the output elastic image by using the time-sequential original elastic image data of past six frames. The numeral value of the image quality in each original elastic image is a numeral value indicating that the image quality is higher as the value thereof is higher, and it is inversely proportional to the rate of content of the artifact contained in the original elastic image. A manner of determining the numeral value representing the image quality will be described later. Furthermore, $T(T-i<T-j; i<j)$ appended to each original elastic image represents a time extending back to a relative past at which the original elastic image concerned is obtained.

When the output elastic image is constructed from the time-sequential original elastic images by using a filter, the output elastic image is constructed so that the following three conditions are satisfied.

(1) Only original elastic images having image quality numeral values not less than a predetermined threshold value are used.

(2) Only when the image quality numeral value of the latest original elastic image is not less than the predetermined threshold value, an output elastic image is constructed from time-sequential original elastic images of past several frames. Accordingly, when the image quality numeral value of the latest original elastic image is less than the threshold value, no output elastic image is constructed, and only a monochrome tomographic image is displayed on CRT 108.

(3) No output elastic image is constructed when it is judged that the latest original elastic image contains artifact. The artifact in the elastic image will be described later.

It is understood from the following description of each acquisition mode that at least one of the image quality and the frame rate of the output elastic image can be fitted to an examination purpose by controlling the threshold value for the image quality numeral value in accordance with the examination purpose when the output elastic image is constructed so as to satisfy the above three conditions.

In the screening mode, a biomedical tissue is roughly pressed and a probe is quickly moved to search a diagnostic site over a broad range area in short time. Therefore, in the screening mode, easy drawing of an image is more strongly required than high image quality. Therefore, in the screening mode, the threshold value for the image quality numeral value is set to a rather low value, whereby the frequency of constructing the output elastic image is increased. That is, the frame rate of the output elastic image is enhanced. Even when a biomedical tissue is quickly displaced due to rough press or quick movement of the probe, the elastic image is easily drawn while following the quick displacement of the biomedical tissue because the frame rate is enhanced. Furthermore, by setting the threshold value of the image quality numeral value to a rather low value, more original elastic images are used to construct the output elastic image, and thus the image quality of the output elastic image is stabilized and image quality from high level to intermediate level can be acquired.

In the screening mode shown in FIG. 5(1), the elastic image constructing portion 106 sets the image quality threshold value to 50, and an output elastic image is constructed by five frames obtained by excluding T-3 having the image quality numeral value less than the threshold value from past six frames. If it is judged that the image quality numeral value of the latest original elastic image T-0 is equal to 65 and not less than the threshold value and contains no artifact, the output elastic image is constructed. In this case, the image quality numeral value of the output elastic image is equal to 76 when it is the additional average of the image quality numeral values of the respective original elastic images. In the just-before step, the image quality numeral value of the original elastic image T-1 is equal to 75 which is not less than the threshold value, and thus if it is judged that no artifact is contained, the output elastic image is constructed. Likewise, in past steps, the output elastic image is constructed in other cases than the original elastic image T-3 in which the image quality numeral value is less than the threshold value. Therefore, the frame rate of the output elastic image is substantially the same rate at which each original elastic image is generated, so that the frame rate of the output elastic image is increased.

On the other hand, in the close examination mode, in order to acquire an elastic image having high image quality and carry out precise examination on a diagnostic site, precise and gentle press is applied to the diagnostic site. Therefore, high image quality is required in the close examination mode. Therefore, in the close examination mode, the threshold value of the image quality numeral value is set to a rather high value, and thus an output elastic image having high image quality is constructed by using only original elastic images of high image quality, whereby the precise examination can be performed. Furthermore, by setting the threshold value of the image quality numeral value to a high value, the frequency of constructing the output elastic image is lowered, so that the frame rate in the close examination mode is lowered. However, in the close examination mode in order to perform the precise examination, the probe 102 is gently pressed against the diagnostic site and thus the displacement of the biomedical tissue is gentle. Accordingly, even when the frame rate is lowered, there is no problem in drawing and diagnosis of the diagnostic site.

In the close examination mode shown in FIG. 5(2), the elastic image constructing portion 106 sets the threshold value to 90, and the output elastic image is constructed by only T-2, T-5 out of past six frames, the image quality numeral values of T-2, T-5 being not less than the threshold value. The image quality numeral value of the latest original elastic image is equal to 65 and thus less than the threshold value, and thus no output elastic image is constructed. Even in the preceding step, the image quality numeral value of the original elastic image T-1 is equal to 75, and thus less than the threshold value, so that no output elastic image is constructed. When the original elastic image T-2 is the latest original elastic image, the image quality numeral value is equal to 90 and thus not less than the threshold value, and thus if it is judged that no artifact is contained, the original elastic image T-5 whose image quality numeral value is not less than the threshold value is contained, and thus the output elastic image is constructed. In this case, the image quality numeral value of the output elastic image is equal to 92.5 when it is equal to the addition average of the image quality numeral values of only T-2, T-5. Furthermore, the frame rate of the output elasticity image is reduced to about ⅓ of the frame rate at which the original elastic image is generated.

The switching operation of the two acquisition modes is carried out by displaying a switching menu on the image and inputting from the operating table 112 by the operator as shown in FIG. 6.

The threshold value for the image quality numeral values in the two acquisition modes may be changed in connection with a target site or a probe being used. The target site and the type of the probe reflect a selected body mark, and thus a body mark 605 shown in FIG. 6 (the figure shows an example that an abdominal part body mark as an example of the body marks is selected and displayed on CRT is displayed), the threshold value may be changed in accordance with the type of the selected body mark. Specifically, when a lacteal gland is targeted, the tissue thereof can be stably distorted and thus high image quality can be easily obtained. Therefore, when the body mark of the lacteal gland is selected, the threshold value in the screening mode can be set to 50, and the threshold value in the close examination mode can be set to 90. When a prostate gland is targeted, it is difficult to press the tissue thereof, and thus the image quality may be lowered. Therefore, when the body mark of the prostate gland is selected, the threshold value in the screening mode can be set to 40 while the threshold value in the close examination mode is set to 75. Furthermore, when an abdominal part is targeted, it is difficult to distort the tissue thereof, and thus the image quality may be lowered. Therefore, when the body mark of the abdominal part is selected, the threshold value in the screening mode may be set to 40 while the threshold value in the close examination mode is set to 60.

Or, the threshold value of each mode may be set by an input from the operating table 112 by the operator.

Next, the manner of determining the numeral value representing the image quality will be described. As described above, the distortion operating portion 105 executes correlation processing on the tomographic image data of two frames, and determines the displacement amount distribution of tomographic image data of the present phase frame from tomographic image data of a past phase frame, and generates it as displacement frame data. The displacement amount distribution is subjected to the spatial differentiation processing to calculate the distortion amount or elastic modulus at each point of the present phase fame and set it as elastic image data. If the displacement amount has a plus gradient, it is a plus distortion amount, and if the displacement amount has a minus gradient, it is a minus distortion amount.

Furthermore, the distortion operating portion 105 calculates the ratio between the number of the tissue elasticity data having plus distortion amounts and the number of tissue elastic data having minus distortion amounts in one fame as an error rate. That is, $$\text{error rate} = (A-B)/(A+B) \times 100(\%) \quad (2)$$

A≡the number of tissue elasticity data having plus distortion amount

B≡the number of tissue elasticity data having minus distortion amount

This error rate is used to judge the presence or absence of artifact in the elastic image. The artifact in the elastic image is connected to the way of pressing to the biomedical tissue, and particularly it is caused by a spike noise occurring when the probe 102 is not constantly pressed against the body being examined 101. For example, a spike noise occurs when the biomedical tissue is upwardly displaced and thus a minus displacement amount occurs in spite of the press of the probe 102 against the biomedical tissue in the downward direction. For example, when this error rate is equal to −20%, that is, the number of tissue elastic data having minus distortion amounts is significantly larger than the number of tissue elastic data having plus distortion amounts, it is judged that the elastic image contains artifact. The original elastic image that is judged to have artifact is excluded from the filter operation to construct an output elastic image.

The image quality numeral value can be calculated from the above respective numeral values according to the following equation (3).

$$\text{Image quality numeral value} = 50x\alpha + 30x\beta + 20x\gamma$$

$\alpha \equiv$ (average of in-frame distortion amount)/normalization constant 1

$\beta \equiv$ (error rate)/normalization constant 2

$\gamma \equiv$ (dispersion of in-frame distortion amount)/normalization constant 3 (3)

Here, the normalization constants 1 to 3 are predetermined constants, and they are constants for normalizing (the average of in-frame distortion amounts), (error rate) and (the dispersion of in-frame distortion amounts). According to the calculation equation (3) above, the image quality numeral value is equal to a value that is not more than 100. The calculation equation (3) above is an example using three kinds of numeral values. However, the image quality numeral value may be calculated by using at least one of the three kinds of numeral values.

The values of the respective coefficients in the calculation equation shown by the calculation equation (3) above for calculating the image quality numeral value may be changed in accordance with the target site and the probe being used as in the case of the above-described threshold value. The target site and the type of the probe reflects the selected body mark, and thus the values of the respective coefficients may be changed in accordance with the selected body mark, for example. Specifically, when the body mark of lacteal gland is selected, the tissue of the lacteal gland is easily softly pressed and thus the value of $\alpha$ is set to a rather high value. Therefore, it is preferable to reduce the coefficient of $\alpha$. Therefore, $$\text{The image quality numeral value} = 40x\alpha + 30x\beta + 30x\gamma \quad (4)$$

Furthermore, when the body mark of prostate gland is selected, it is difficult to press the prostate gland, and thus it is preferable that the respective values of $\alpha$, $\beta$ and $\gamma$ are estimate with excellent balance. Therefore, $$\text{The image quality numeral value} = 50x\alpha + 25x\beta + 25x\gamma \quad (5)$$

Furthermore, when the body mark of an abdominal part is selected, the tissue of the abdominal part is uniform, but it is slightly solid, so that the value of $\alpha$ is rather low. Therefore, it is preferable to increase the coefficient of $\alpha$. Therefore, $$\text{Image quality numeral value} = 60x\alpha + 30x\beta + 10x\gamma \quad (6)$$

As described above, according to this embodiment, when the output elastic image is constructed by using plural time-sequential original elastic images, plural acquisition modes which are different in at least one of the image quality and the frame rate of the output elastic image can be provided by controlling the image quality threshold value of the original elastic images adopted to construct the output elastic image, and the acquisition modes can be selectively used in accordance with the examination purpose.

The foregoing description relates to the respective embodiments of the ultrasonic diagnostic apparatus of the present invention. However, the ultrasonic diagnostic apparatus of the present invention is not limited to the content disclosed in the description of the embodiments, and other embodiments may be used in consideration of the subject matter of the present invention.

For example, the respective embodiments described above may be independently carried into effect, and the frame rate of the elastic image in the screening mode may be further enhanced by combining any two or more embodiments. Or, the image quality of the close examination mode may be further enhanced.

Specifically, at least by increasing the correlation window for calculating the tissue elasticity amount, broadening the search range for calculating the tissue elasticity amount or reducing the moving interval of the search range for calculating the tissue elasticity amount in the close examination mode as compared with the screening mode, plural original elastic images are obtained, the image quality numeral value representing the image quality is determined every original elastic image, and an elastic image having higher image quality and a lower frame rate than that in the screening mode can be output by using one or more original elastic image having a higher image quality numeral value not less than the threshold value than that in the screening mode.

Or, at least by reducing the correlation window for calculating the tissue elasticity amount, narrowing the search range for calculating the tissue elasticity amount or broadening the moving interval of the search range for calculating the tissue elasticity amount in the screening mode as compared with the close examination mode, plural original elastic images are obtained, the image quality numerical number representing the image quality is determined every original elastic image, and an elastic image having lower image quality and a higher frame rate than that in the close examination mode can be output by using one or more original elastic images having a lower image quality numeral value not less than the threshold value than that in the close examination.

Furthermore, the frame rate may be enhanced by contracting the frame width of the elastic image in at least one of the scan line direction and the raster direction as the screening mode.

Plural correlation windows may be set at the same time and the close examination mode and the screening mode may be executed on the same screen.

Furthermore, there may be used a mode in which the frame rate, the threshold value or the like is stepwise varied as the position shifts to an indicated site on the screen. That is, the periphery of the indicated range of the screen is gradually varied to the close examination mode. It is needless to say that the processing of specifying the diagnostic site and then switching to the close examination mode can be performed in such a mode.

FIG. 1
101 ... BODY BEING EXAMINED
102 ... PROBE
103 ... ULTRASONIC TRANSMITTING/RECEIVING PORTION
104 ... TOMOGRAPHIC IMAGE CONSTRUCTING PORTION
105 ... DISTORTION OPERATING PORTION
106 ... ELASTIC IMAGE CONSTRUCTING PORTION
107 ... COMBINING PORTION
110 ... COLOR SCALE CONSTRUCTING PORTION
111 ... CONTROL OPERATING PORTION
112 ... OPERATING TABLE

FIG. 2
203 ... ELASTIC IMAGE
201 ... TOMOGRAPHIC IMAGE

FIG. 3
301 ... ULTRASONIC SIGNAL
302 ... TISSUE ELASTICITY SIGNAL
(a) CLOSE EXAMINATION MODE
(b) SCREENING MODE (EQUALITY)
(c) SCREENING MODE (INTERMEDIATE DEPTH PORTION)
(d) SCREENING MODE (DEEP DEPTH PORTION)

FIG. 5
SCREENING MODE
OUTPUT FRAME=IMAGE QUALITY 65, ....
CLOSE EXAMINATION MODE
OUTPUT FRAME=IMAGE QUALITY 65, ....

FIG. 6
MODE: 1 SCREENING MODE, 2. CLOSE EXAMINATION MODE

The invention claimed is:

1. An ultrasonic diagnostic apparatus comprising:
tomographic image acquisition means for transmitting ultrasonic waves from a probe to a body being examined and receiving the reflection echo signal corresponding to the transmission of the ultrasonic waves to obtain a tomographic image;
elastic image acquisition means having a first acquisition mode for determining a tissue elasticity amount of a biomedical tissue of the body being examined on the basis of the reflection echo signal to acquire an elastic image; and
display means for displaying at least the elastic image, characterized in that the elastic image acquisition means further has a second acquisition mode, and the elastic image acquired in the second acquisition mode is different in image quality from the elastic image acquired in the first acquisition mode,
wherein the elastic image acquisition means is configured so that the image quality of the elastic image based on the second acquisition mode is reduced to be less than the image quality of the elastic image based on the first acquisition mode, and
wherein the elastic image acquisition means is configured so that the frame rate of the elastic image acquired in the second acquisition mode is higher than the frame rate of the elastic image acquired in the first acquisition mode.

2. The ultrasonic diagnostic apparatus according to claim 1, wherein the elastic image acquisition means calculates, when one output elastic image is constructed by using plural time-sequential original elastic images, an image quality numerical value representing the image quality of each original elastic image, and constructs the output elastic image by using only the original elastic images whose image quality numerical values are equal to a predetermined threshold value or more, and the elastic image acquisition means is configured so that the threshold value used in the second acquisition mode is smaller than the threshold value used in the first acquisition mode.

3. The ultrasonic diagnostic apparatus according to claim 2, wherein the elastic image acquisition means carries out at least one of the calculation of the image quality numerical value and the setting of the predetermined threshold value in accordance with a selected body mark.

4. The ultrasonic diagnostic apparatus according to claim 1, wherein the elastic image acquisition means acquires plural original elastic images at least by making larger a correlation window for calculating the tissue elasticity amount, broadening a search range for calculating the tissue elasticity amount or narrowing a moving interval of the search range for calculating the tissue elasticity amount in the first acquisition mode as compared with the second acquisition mode, an image numerical value representing the image quality of an original elastic image is determined every original elastic image, an elastics image having higher image quality than that in the second acquisition mode is output by using one or more original elastic images having image numerical values not less than a threshold value higher than that of the second acquisition mode.

5. The ultrasonic diagnostic apparatus according to claim 1, wherein the elastic image acquisition means acquires plural original elastic images at least by making smaller a correlation window for calculating the tissue elasticity amount, narrowing a search range for calculating the tissue elasticity amount for calculating the tissue elasticity amount or broadening a moving interval of the search range for calculating the tissue elasticity amount in the second acquisition mode as compared with the first acquisition mode, an image quality numeral value representing the image quality of each original elastic image is determined every original elastic image, and an elastic image having lower image quality than that in the first acquisition mode is output by using one or more original elastic images whose image quality numerical values are not less than a threshold value lower than that of the first acquisition mode.

6. The ultrasonic diagnostic apparatus according to claim 1, wherein the tissue elasticity amount is a distortion determined by spatially differentiating the displacement of the biomedical tissue or an elastic modulus obtained by dividing a stress measured through means for measuring pressure applied to the biomedical tissue by the distortion concerned.

7. The ultrasonic diagnostic apparatus according to claim 1, further comprising switching means for switching the first acquisition mode and the second acquisition mode to each other, and the elastic image acquisition means switches the acquisition mode in response to an instruction from the switching means.

8. An ultrasonic diagnostic apparatus comprising:
tomographic image acquisition means for transmitting ultrasonic waves from a probe to a body being examined and receiving the reflection echo signal corresponding to the transmission of the ultrasonic waves to obtain a tomographic image;
elastic image acquisition means having a first acquisition mode for determining a tissue elasticity amount of a biomedical tissue of the body being examined on the basis of the reflection echo signal to acquire an elastic image; and
display means for displaying at least the elastic image, characterized in that the elastic image acquisition means further has a second acquisition mode, and the elastic image acquired in the second acquisition mode is different in image quality from the elastic image acquired in the first acquisition mode, wherein the elastic image acquisition means is configured so that the image quality of the elastic image based on the second acquisition mode is reduced to be less than the image quality of the elastic image based on the first acquisition mode, wherein the elastic image acquisition means is configured so that a thinning out amount in a scan line direction for the calculation of the tissue elasticity amount based on the second acquisition mode is larger than the thinning-out amount in a scan line direction for the calculation of the tissue elasticity amount based on the first acquisition mode.

9. The ultrasonic diagnostic apparatus according to claim 8, wherein the elastic image acquisition means is configured so that the precision of the tissue elasticity amount calculated in the second acquisition mode is lower than the precision of the tissue elasticity amount calculated in the first acquisition mode.

10. The ultrasonic diagnostic apparatus according to claim 8, wherein the elastic image acquisition means is configured so that a spatial resolution of the elastic image acquired in the second acquisition mode is lower than a spatial resolution of the elastic image acquired in the first acquisition mode.

11. The ultrasonic diagnostic apparatus according to claim 8, wherein the elastic image acquisition means is configured so that a correlation window for calculating the tissue elasticity amount used in the second acquisition mode is smaller than the correlation window used in the first acquisition mode.

12. The ultrasonic diagnostic apparatus according to claim 8, wherein the elastic image acquisition means is configured so that a search range for calculating the tissue elasticity amount used in the second acquisition mode is narrower than the search range used in the first acquisition mode.

13. The ultrasonic diagnostic apparatus according to claim 8, wherein the elastic image acquisition means is configured so that a moving interval of a search range for calculating the tissue elasticity amount used in the second acquisition mode is broader than the moving interval used in the first acquisition mode.

14. The ultrasonic diagnostic apparatus according to claim 8, wherein the thinning-out of the tissue elasticity amount is carried out in a scan line direction.

15. The ultrasonic diagnostic apparatus according to claim 14, wherein the calculation of the tissue elasticity amount is more densely carried out at a portion in the scan line direction than at the other portion.

16. The ultrasonic diagnostic apparatus according to claim 15, wherein the portion at which the calculation of the tissue elasticity amount is densely carried out is a substantially center portion in the scan line direction.

17. The ultrasonic diagnostic apparatus according to claim 14, wherein the thinning-out of the tissue elasticity amount is carried out in a raster direction.

18. The ultrasonic diagnostic apparatus according to claim 8, wherein the thinning-out of the tissue elasticity amount is substantially equally carried out in the scan line direction.

* * * * *